(12) United States Patent
Farrer

(10) Patent No.: US 9,788,713 B2
(45) Date of Patent: *Oct. 17, 2017

(54) OPHTHALMIC METHOD FOR SHAPE DETERMINATION AND MODIFICATION

(71) Applicant: AMO Wavefront Sciences LLC., Santa Ana, CA (US)

(72) Inventor: Stephen W. Farrer, Albuquerque, NM (US)

(73) Assignee: AMO Wavefront Sciences LLC., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,171

(22) Filed: Mar. 10, 2014

(65) Prior Publication Data

US 2014/0253878 A1    Sep. 11, 2014

Related U.S. Application Data

(62) Division of application No. 12/960,252, filed on Dec. 3, 2010, now Pat. No. 8,709,002.

(Continued)

(51) Int. Cl.
*A61B 18/18* (2006.01)
*A61B 3/00* (2006.01)
(Continued)

(52) U.S. Cl.
CPC ............ *A61B 3/0025* (2013.01); *A61B 3/107* (2013.01); *A61F 9/00804* (2013.01);
(Continued)

(58) Field of Classification Search
CPC ..... A61B 3/0025; A61B 3/107; A61B 3/1005; A61B 3/11–3/112; G01B 11/25
(Continued)

(56) References Cited

U.S. PATENT DOCUMENTS 4,761,071 A    8/1988    Baron
5,886,767 A    3/1999    Snook
(Continued)

FOREIGN PATENT DOCUMENTS

NL    WO 2009056161 A1 *    5/2009    ............. A61B 3/107

OTHER PUBLICATIONS

Fazekas Z., et al., "Specular Surface Reconstruction for Multi-Camera Corneal Topographer Arrangements," 30th Annual International IEEE EMBS Conference, Vancouver, British Columbia, Canada, Aug. 20-24, 2008, pp. 2254- 2257.
(Continued)

*Primary Examiner* — Nathan J Jenness
(74) *Attorney, Agent, or Firm* — Abbott Medical Optics Inc.

(57) ABSTRACT

Systems and methods for modifying an eye including a light source with light elements, a photodetector producing a signal representing images of the light elements and corresponding to locations on an ocular surface, an optical system directing light from the light elements reflected by the ocular surface onto the photodetector, a memory including code for processing the signal, and a processor for executing the code and outputting shape data for use in calculating a treatment plan for the eye. The code includes instructions for determining the shape data based on a combination of zonal reconstruction and polynomial fitting using the plurality of images.

4 Claims, 6 Drawing Sheets

Related U.S. Application Data

(60) Provisional application No. 61/266,951, filed on Dec. 4, 2009.

(51) Int. Cl.
    *A61B 3/107*     (2006.01)
    *A61F 9/008*     (2006.01)
    *A61F 9/013*     (2006.01)

(52) U.S. Cl.
    CPC .......... *A61F 9/00827* (2013.01); *A61F 9/013* (2013.01); *A61F 2009/00844* (2013.01); *A61F 2009/00872* (2013.01); *A61F 2009/00882* (2013.01)

(58) Field of Classification Search
    USPC ..................... 606/4, 5; 351/159.23, 206, 212
    See application file for complete search history.

(56) References Cited

U.S. PATENT DOCUMENTS

| | | | |
|---|---|---|---|
| 7,023,432 | B2 | 4/2006 | Fletcher et al. |
| 7,365,893 | B2 | 4/2008 | Chernyak et al. |
| 7,976,163 | B2 | 7/2011 | Campbell et al. |
| 7,988,293 | B2 | 8/2011 | Raymond et al. |
| 2006/0126019 | A1 | 6/2006 | Liang et al. |
| 2006/0158612 | A1* | 7/2006 | Polland et al. ............... 351/206 |
| 2006/0215114 | A1 | 9/2006 | Flachenecker |
| 2007/0291228 | A1 | 12/2007 | Huang et al. |
| 2009/0161090 | A1 | 6/2009 | Campbell et al. |
| 2009/0175525 | A1 | 7/2009 | Farrer et al. |
| 2012/0172854 | A1* | 7/2012 | Raymond ............... A61F 9/008 606/5 |

OTHER PUBLICATIONS

Dai G., Wavefront optics for Vision Correction, SPIE, 2008.
"International Preliminary Report on Patentability and Written Opinion for Application No. PCT/US2010/058956, mailed on Jun. 5, 2012, 7 pages".
International Search Report for Application No. PCT/US2010/058956. mailed on Mar. 4, 2011, 2 pages.
Ortiz S., et al., "Three-dimensional Ray Tracing on Delaunay-based Reconstructed Surfaces," Applied Optics, 2009, vol. 48 (20), pp. 3886-3893.
Southwell W.H., "Wave-Front Estimation from Wave-Front Slope Measurements," Journal of the Optical Society of America, 1980, vol. 70 (8), pp. 998-1006.

* cited by examiner

OPHTHALMIC METHOD FOR SHAPE DETERMINATION AND MODIFICATION

CROSS-REFERENCE TO RELATED APPLICATION

This application is a divisional application and claims priority to U.S. application Ser. No. 12/960,252, entitled "Ophthalmic Systems and Related Methods", filed on Dec. 3, 2010, which claims priority to U.S. Provisional No. 61/266,951, entitled "Ophthalmic Systems and Related Methods", filed on Dec. 4, 2009, the entire contents of which are hereby incorporated by reference for all purposes as if fully set forth herein.

BACKGROUND OF THE INVENTION

Field of the Invention

The present invention relates generally to systems and methods for measuring and treating an eye, and more specifically to systems and methods for determining the shape of an ocular surface and using the determined shape in treating and/or improving vision of the eye.

Background

One of the interesting features of spot based corneal topography is that the source locations can be arranged so that after reflection of the cornea, the spots form a nearly uniform grid. However, due to corneal irregularities and various corneal shapes, a perfectly uniform grid is not guaranteed and in practice never achieved; leading to the problem of working with arbitrary point clouds of data. While modal reconstructors (for example, based on Zernike Polynomials) can handle arbitrary point locations, for surfaces containing high spatial frequency content modal reconstructors do not have sufficient fidelity unless extended to include higher orders.

Accordingly, methods and systems are desired that incorporate more robust reconstructors. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards systems and methods of direct solution zonal reconstruction that do not rely on a uniform grid of points for reconstruction, unlike other common wavefront reconstruction methods based on iterative methods in uniform space. Embodiments of the present invention are directed to systems and methods for determining the shape of ocular surfaces and using the determined shape for treating and/or improving vision of the eye, for example, by providing input for determination of a treatment plan in a corneal refractive procedure, such as laser assisted in-situ keratomilieusis (LASIK), photorefractive keratectomy (PRK), laser assisted sub-epithelium keratomileusis (LASEK), corneal implants, corneal onlays, intrastromal modifications, and the like.

In one embodiment, a system is provided having a light source including a plurality of light elements, a photodetector, an optical system for directing light from the light elements reflected by a surface of the eye onto the photodetector, a memory including programming code for processing the signal produced by the photodetector, and a processor for executing the programming code and outputting shape data for use in calculating a treatment plan for a corneal refractive procedure on the eye. The photodetector is configured to produce a signal representing a plurality of images of at least some of the plurality of light elements, each image corresponding to a location on the surface of the eye. The programming code includes instructions for determining the shape data based on a combination of zonal reconstruction and polynomial fitting using the plurality of images.

In another embodiment, a method is provided for shape determination of a surface of an eye. The method includes sensing a light pattern based on a plurality of images reflected from the surface of the eye, each image corresponding to a location on the surface of the eye, and determining shape data corresponding to the surface of the eye based on a combination of zonal reconstruction and polynomial fitting using the plurality of images.

BRIEF DESCRIPTION OF THE DRAWINGS

In the drawings, wherein like reference numerals refer to similar components.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The present invention provides a direct solution zonal reconstruction method that does not rely on a uniform grid of points for reconstruction, unlike other common wavefront reconstruction methods based on iterative methods in uniform space. Embodiments of the present invention are directed to systems and methods for determining the shape of ocular surfaces and using the determined shape for treating and/or improving vision of the eye, for example, by providing input for determination of a treatment plan in a corneal refractive procedure, such as LASIK, PRK, LASEK, and the like.

Figure 1:
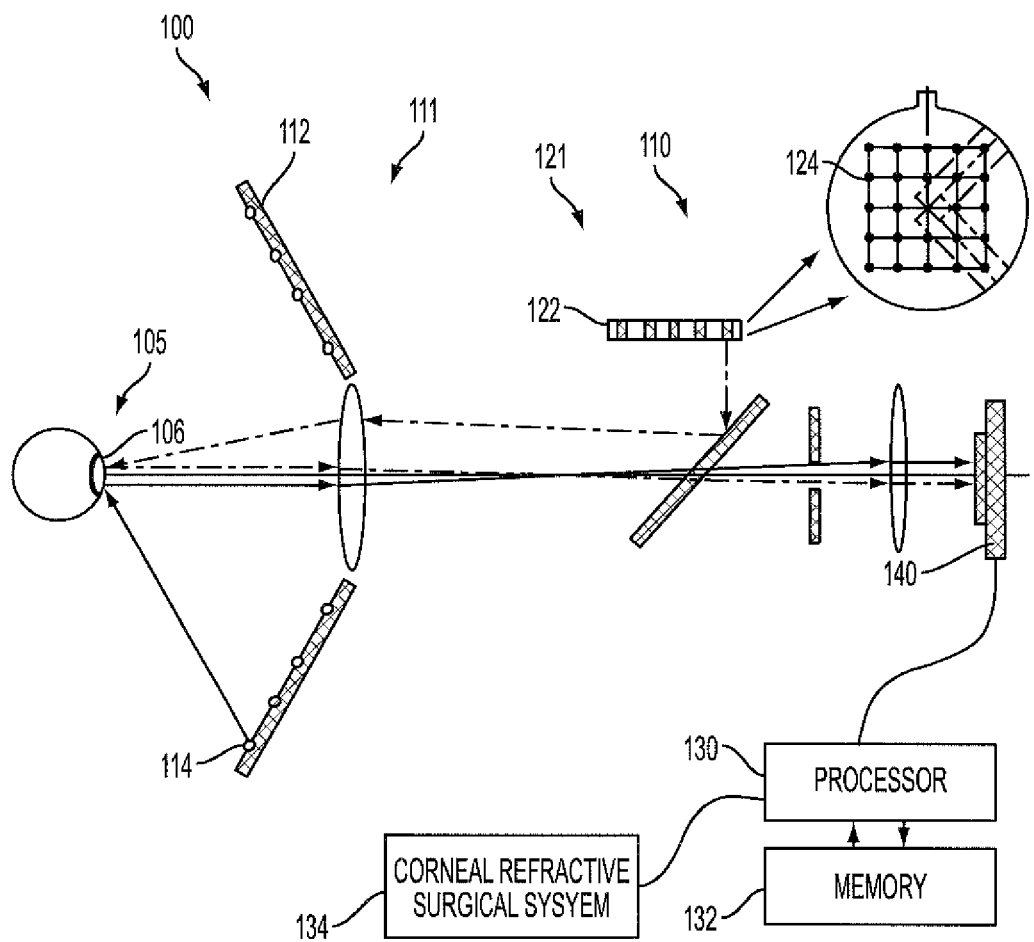
FIG. 1 is a diagram of a system for measuring an eye in accordance with one embodiment.

Referring to FIG. 1, in certain embodiments of the present invention, a system 100 for measuring an eye 105 comprises a topography system 110 that includes a first topographer 111 comprising a first light source 112 having a plurality of first light elements 114 (e.g., LEDs or the like) and a second topographer 121 comprising a second light source 122 having a plurality of second light sources 124 (e.g., LEDs or the like). In the illustrated embodiment, first light source 112 is a cone or other suitable surface shape disposed near eye 105 and configured to provide a profile of an outer portion of a corneal surface 106 of eye 105, while second light source is a so-called Helmholtz light source. System 100 may also include other optical diagnostic systems, such as an aberrometer for measuring aberrations of the total eye 105, visualization targets, iris or retinal imaging systems, and the like. Features of system 100 and topography system 110 may be similar or identical to at least some of those disclosed in U.S. Patent Publication Numbers 20090161090 and 20090175525, which are herein incorporated by reference in their entirety as if fully set forth herein.

System 100 further comprises a computer and/or processor 130 operably coupled to a memory 132, as well as additional input and output devices such as monitors, keyboard, control devices, and the like. In the illustrated embodiment, processor 130 is operably coupled to a photodetector 138, which may be a CCD (charge coupled device) or other suitable device. Photodetector 138 is configured to receive light from the first and second light sources 112, 122. System 100 may be configured so that both topographers 111, 121 utilize photodetector 138.

During operation, light elements 114, 124 are reflected from corneal surface 106 to form a detector image or signal on photodetector 140 comprising a plurality of individual images of light elements 114, 124. Knowing the geometry of system 100, the location of these individual images on photodetector 140 may be used to determine locations on the corneal surface 106 from which the light beam forming each image was reflected. The individual images may also be used to calculate or estimate slope and/or higher derivative at each location on corneal surface 106. Because the corneal shape is unknown and because the shape affects the location of the light reflected from each light element 114, 124, accurate determination of the corneal shape may require iterative processing of the data provided by the individual images created on photodetector 140.

The individual images may be in the form of spots or blobs extending over a plurality of pixels of photodetector 140. Various routines known in the art may be used to determine an image coordinate for each spot image. In addition, routines known in the art may be used to associate each spot image with a particular light element 114, 124 of topographer 110, 120 and to eliminate certain spot images when required and/or desired.

System 100 may be a stand alone ophthalmic diagnostic system or instrument. Alternatively, system 100 may include, and/or be directly or functionally coupled to, a corneal refractive surgical system 140, for example, that is configured to provide a LASIK refractive procedure. Processor 130 is generally configured to provide output, based on images of light elements 114 and/or 124, that is in the form of a treatment plan and/or surface shape data that may be used to calculate a treatment plan (e.g., for refractive correction of ocular aberrations).

Figure 2:
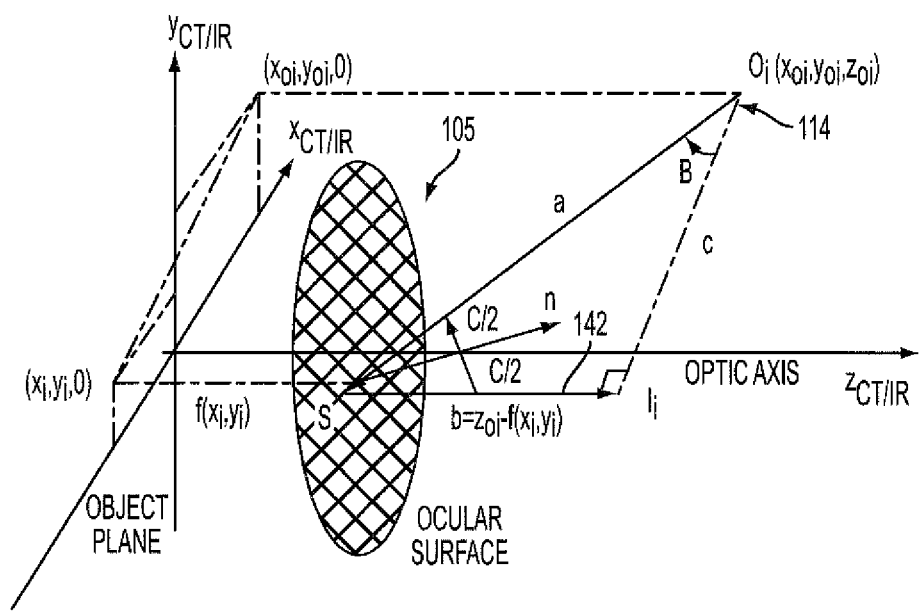
FIG. 2 is a diagram of an input light element and an eye illustrating a relationship of a light beam reflected by the cornea of the eye with respect to a coordinate system in accordance with one embodiment.

Referring to FIG. 2, a coordinate system is shown for eye 105 along with an exemplary input light element 114 and a corresponding light beam 142 reflected by the cornea of eye 105. In this embodiment, the coordinate system is aligned with an optic axis of eye 105. Although not shown in FIG. 2, system 100 (FIG. 1) may be located to the right of eye 105, such as depicted in FIG. 1.

Figure 3:
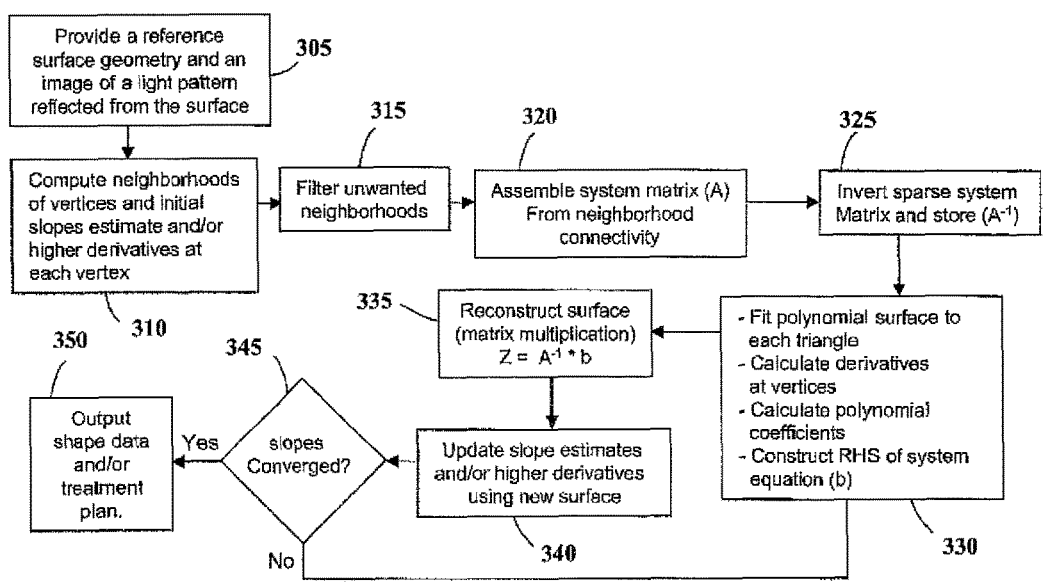
FIG. 3 is a flow diagram of a method for determining a shape of a surface of the eye and/or providing a treatment plan for a refractive procedure in accordance with one embodiment.

Referring to FIG. 3, in certain embodiments, a method 300 is used for determining a shape of a surface of eye 105 and/or providing a treatment plan for a refractive procedure. Method 300 may be used in conjunction with either or both topographers 111, 121, or with any topography system configured to produce input image data suitable for use in method 300. Referring also to FIG. 1, method 300 will be discussed in conjunction with first and second light elements 114, 124; however, method 300 may also be used additionally or alternatively in conjunction with other light sources and/or topographers.

Method 300 comprises an element 305 of providing an initial reference shape or geometry of corneal surface 106 of eye 105 and providing an image of a light pattern on photodetector 140 from light from light elements 114, 124 reflected by corneal surface 106. Method 300 also comprises an element 310 of determining or computing a plurality of neighborhoods of vertices representing various area segments of the surface of eye 105, and determining one or more slopes and/or higher derivatives (e.g. $d/dx^2$, $d/dy^2$) at each vertex. Method 300 also comprises an element 315 of filtering out unwanted neighborhoods. Method 300 further comprises an element 320 of producing a system matrix A based on the vertices included in each neighborhood. Method 300 additionally comprises an element 325 of inverting the system matrix A to provide the inverse matrix $A^{-1}$. Method 300 also comprises an element 330 of fitting an equation having a plurality of parameters and parameter coefficients to each neighborhood, estimating values for one or more derivatives for each vertex based on the equations, and providing difference matrix b representing relative distances between various pairs of vertices within each neighborhood. Method 300 further comprises an element 335 of reconstructing a new geometry of the vertices representing a new estimate of a shape of the surface of eye 105. Method 300 additionally comprises an element 340 of updating values for the slopes and/or higher derivatives at each vertex in each neighborhood. Method 300 further comprises an element 345 of evaluating converges of surface shape estimate. Method 300 also comprises an element 350 of outputting shape data and/or a treatment plan based on the shape data if the shape estimate has sufficiently converged. Otherwise, elements 330 to 340 may be repeated by replacing the reference geometry and the initial vertex slopes and/or higher derivatives with at least some of the new geometry and new slope and/or higher derivatives values for each vertex in each neighborhood.

In element 305, an initial estimate is made of the shape or geometry of corneal surface 106. The surface may be a front and/or rear surface of the cornea of eye 105, or some other surface within eye 105, such as an anterior or posterior surface of the natural crystalline lens or and implanted devices such as an intraocular lens. The initial shape estimate may be made from some or all of the spot images created on photodetector 140 by light elements 114, 124. Alternatively, data from other instruments may be used to provide an initial estimate of the corneal surface 106 shape, or the initial estimate may be a surface having a predetermined shape, for example, a plane, a sphere having a predetermined curvature, or an aspheric surface characterized by a predetermined curvature and conic constant.

Figure 4:
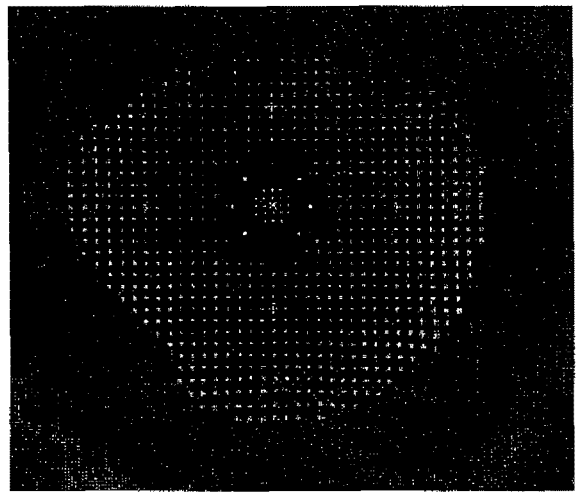
FIG. 4 is an image of a light pattern of spots projected onto an eye in accordance with one embodiment.

Referring to FIG. 4, an exemplary light pattern of spots on photodetector 140 is illustrated for light elements 114, 124. Four of the light elements 114 are in the form of crosses and may be used as a fiducial to aid in associating each light spot with a corresponding element 114 on first light source 112.

In element 310, a plurality of neighborhoods is defined comprising three or more vertices representing the location of three or more of the spot images from the photodetector 140 signal. The various neighborhoods may be defined to represent a predetermined or desired portion of corneal surface 106. Various criteria may be used to assign each of the plurality of neighborhoods. For example, a Delaunay triangulation may be used to assign the individual neighborhoods. Based on the initial geometry, an initial surface slope and/or higher derivatives at each vertex are also determined, the initial slope and/or higher derivatives generally being along two orthogonal axes.

Figure 5:
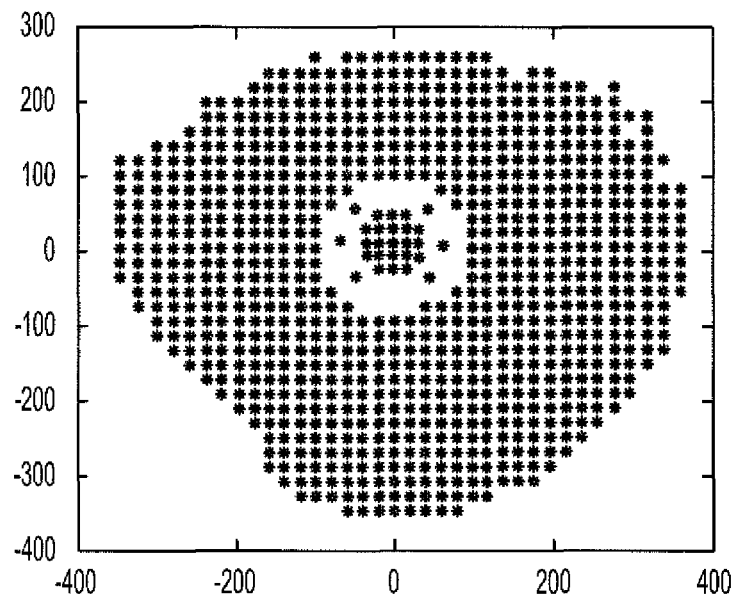
FIG. 5 is an illustration of a location of the pattern of spots shown in FIG. 4 illustrating in accordance with one embodiment.
Figure 6:
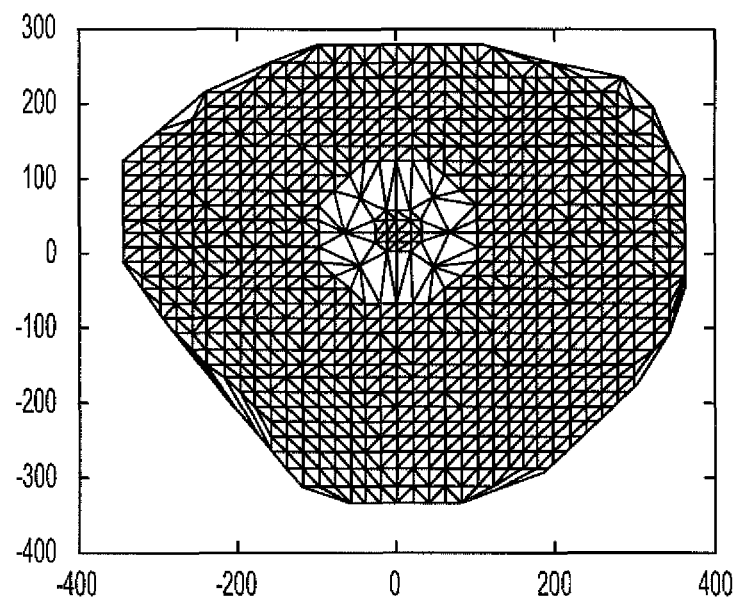
FIG. 6 is an illustration of a Delaunay triangulation of the pixel representation shown in FIG. 5 in accordance with one embodiment.

Referring to FIG. 5, the vertices associated with reflected spots from light elements 114, 124 are shown as stars. Referring to FIG. 6, a plurality of triangular neighborhoods is shown, the triangle being defined by lines between sets of three vertices.

Figure 7:
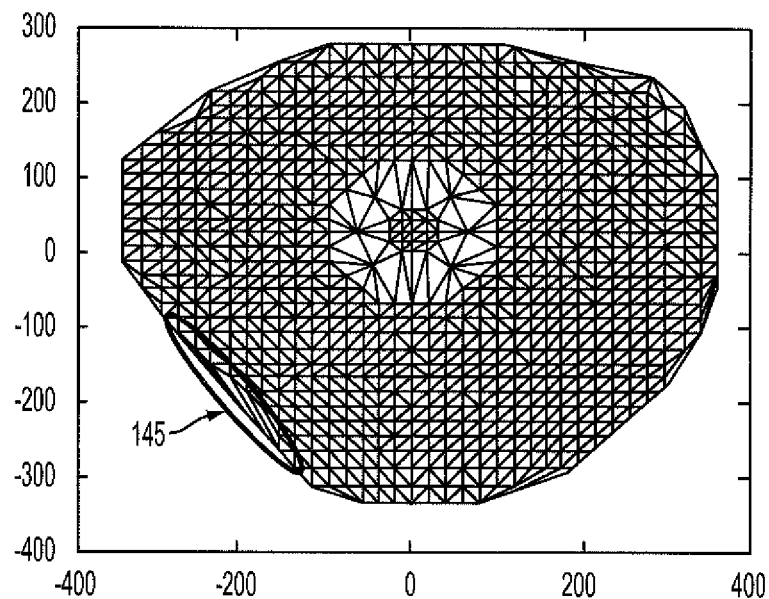
FIG. 7 is an illustration of the Delaunay triangulation shown in FIG. 5 emphasizing a triangular neighborhood in accordance with one embodiment.
Figure 8:
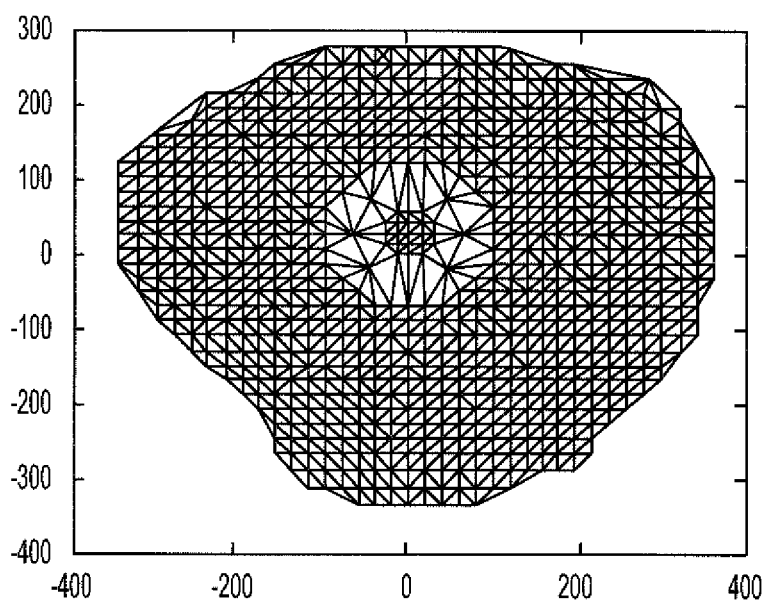
FIG. 8 is an illustration of the Delaunay triangulation shown in FIG. 5 with modified triangular neighborhoods in accordance with one embodiment.

Referring to FIGS. 7 and 8, in element 315, a filter is used to eliminate some of triangular neighborhoods shown in FIG. 6. In this case, an area 145 is an edge of image that was interrupted by a shadowing caused by the subject's nose. The neighborhoods defined in area 145, as well as various other smaller areas about the periphery of the image in FIG. 7, are characterized by triangles with at least one very small vertex angle. By simply eliminating triangular neighborhoods with vertex angles below a predetermined minimum, a modified set of neighborhoods is produced, as shown in FIG. 8.

In element 320, one or more of the neighborhoods may be filtered out or eliminated based on some predetermined criteria, for example, eliminating certain Delaunay triangles having angles that are less than a predetermined threshold angle.

In element 320, the neighborhoods defined in elements 310, 320 and associated vertices are used to define the system matrix A. The system matrix A may include a difference along the z-axis between each pair of vertices in each and every neighborhood, whereby the matrix is a square matrix having a dimension of n×n, where n is equal to the sum of the number of vertices differences in each neighborhood. For example, if Delaunay triangulation is used, the matrix dimension would be three (the number of vertex pair in each of the triangular neighborhoods) times the number of neighborhoods used. It will be appreciated that the dimension will be larger than the total number of vertices defined in the photodetector image, since each vertex is generally contained in more than one neighborhood.

In element 325, the system matrix A is inverted. Since each row of the matrix will only have a few non-zero values, system matrix A is sparse and rank deficient, but may be inverted using a pseudo-inverse (e.g., by Singular Value Decomposition or some equivalent method), allowing for a least squares solution to the overall system equation and the surface values at all the vertices.

In element 330, system constraints are defined by which a new surface shape may be calculated. First, a function is selected to characterize the shape of corneal surface 106 at each neighborhood. The function has a plurality of parameters, where each parameter has a coefficient that to be solved for. Any of a variety of functions may be selected, such as a polynomial function, a Gaussian function, a trigonometric function, a Zernike polynomial, etc. In certain embodiments, the function is a second order polynomial function:

$$z_i = A_i x_{ij}^2 + B_i x_{ij} y_{ij} + C_i y_{ij}^2 + D_i x_{ij} + E_i y_{ij} + F_i, \quad (1)$$

where x and y are axes of a plane about which the corneal surface is disposed, z is an axis perpendicular to the plane, i is an integer designating each of the neighborhoods, j is an integer designating each vertex defined by the corneal surface 106 and the light elements 114, 124, and $A_i$–$F_i$ are constants to be determined in element 330 of method 300.

Once a function has been selected, a predetermined number of derivatives are taken, where the number of derivatives is preferably sufficient to provide at least as many equations between all the vertices in each neighborhood as there are coefficient in each function. For example, if neighborhoods are defined by triangles and the second order polynomial function above used, there are 3 vertices and 6 coefficients (5 of which are ultimate used). Thus, enough equations may be provided by selecting two partial derivatives in x and y:

$$\frac{\partial z_i}{\partial y} = 0 + B_i x_{ij} + 2C_i + 0 + E_i$$

$$\frac{\partial z_i}{\partial x} = 2A_i x_{ij} + B_i y_{ij} + D_i$$

Thus, the coefficients $A_i$–$F_i$ may be solved for each neighborhood by the matrix equation:

$$\begin{vmatrix} 2x_{i1} & y_{i1} & 0 & 1 & 0 \\ 0 & x_{i1} & 2y_{i1} & 0 & 1 \end{vmatrix} \begin{vmatrix} A \\ B \\ C \\ D \\ E \end{vmatrix} = \begin{vmatrix} \frac{\partial z_{ij}}{\partial x} \\ \frac{\partial z_{ij}}{\partial y} \end{vmatrix} \quad (2)$$

In certain embodiments, it has been found advantageous to characterize each neighborhood by a third order polynomial:

$$z_i = A_i X_{ij}^3 + B_i x_{ij}^2 y_{ij} + C_i x_{ij} y_{ij}^2 + D_i y_{ij}^3 + E_i + F_i x_{ij} y_{ij} + G_i y_{ij}^2 + H_i x_{ij} + I_i y_{ij} + J_i \quad (3)$$

where $A_i$–$J_i$ are constants to be determined in element 330 of method 300. It has been discovered that a third order polynomial may surprisingly converge much more quickly, require less total computing time, and be better able to accurately determine surfaces having higher frequency content than does a second order polynomial equation. In this case, a desired number of equations to solve for $A_i$–$J_i$ may be obtained, when the neighborhood has three vertices, by selecting the five partial derivatives:

$$\frac{\partial z_i}{\partial x}, \frac{\partial z_i}{\partial y}, \frac{\partial^2 z_i}{\partial x^2}, \frac{\partial^2 z_i}{\partial y^2}, \frac{\partial^2 z_i}{\partial x \partial y},$$

whereby the coefficients $A_i$–$J_i$ may be solved for each neighborhood by the matrix equation:

$$\begin{vmatrix} 3x^2 & 2xy & y^2 & 0 & 2x & y & 0 & 1 & 0 \\ 0 & x^2 & 2xy & 3y^2 & 0 & x & 2y & 0 & 1 \\ 6x & 2y & 0 & 0 & 2 & 0 & 0 & 0 & 0 \\ 0 & 0 & 2x & 6y & 0 & 0 & 2 & 0 & 0 \\ 0 & 2x & 2y & 0 & 0 & 1 & 0 & 0 & 0 \end{vmatrix} \begin{vmatrix} A \\ B \\ C \\ D \\ E \\ F \\ G \\ H \\ I \end{vmatrix} = \begin{vmatrix} \frac{\partial z_{ij}}{\partial x} \\ \frac{\partial z_{ij}}{\partial y} \\ \frac{\partial^2 z_{ij}}{\partial x^2} \\ \frac{\partial^2 z_{ij}}{\partial y^2} \\ \frac{\partial^2 z_{ij}}{\partial xy} \end{vmatrix}$$

In element 335 of method 300, having solved for the coefficients for each neighborhood, a new surface is calculated by minimizing the global difference between the assumed model and the surface results using the matrix equation $Z=A^{-1}*b$, where Z is a matrix of new z-coordinates. When the neighborhoods are triangles and the vertices are characterized by the second degree polynomial above, the b matrix is defined by the functions on the Right Hand Side (RHS) of the following set of equations:

(System)(RHS)

$z_{11} - z_{12} = A_1(x_{11}^2 - x_{12}^2) + B_1(x_{11}y_{11} - x_{12}y_{12}) +$
$\qquad C_1(y_{11}^2 - y_{12}^2) + D_1(x_{11} - x_{12}) + E_1(y_{11} - y_{12})$ $z_{12} - z_{13} = A_1(x_{12}^2 - x_{13}^2) + B_1(x_{12}y_{12} - x_{13}y_{13}) +$
$\qquad C_1(y_{12}^2 - y_{13}^2) + D_1(x_{12} - x_{13}) + E_1(y_{12} - y_{13})$ $z_{13} - z_{11} = A_1(x_{13}^2 - x_{11}^2) + B_1(x_{13}y_{13} - x_{11}y_{11}) +$
$\qquad C_1(y_{13}^2 - y_{11}^2) + D_1(x_{13} - x_{11}) + E_1(y_{13} - y_{11})$

...

$z_{i1} - z_{i2} = A_i(x_{i1}^2 - x_{i2}^2) + B_i(x_{i1}y_{i1} - x_{i2}y_{i2}) +$
$\qquad C_i(y_{i1}^2 - y_{i2}^2) + D_i(x_{i1} - x_{i2}) + E_i(y_{i1} - y_{i2})$

...

$z_{N3} - z_{N1} A_N(x_{N3}^2 - x_{N1}^2) + B_N(x_{N3}y_{N3} - x_{N1}y_{N1}) +$
$\qquad C_N(y_{N3}^2 - y_{N1}^2) + D_N(x_{N3} - x_{N1}) + E_N(y_{N3} - y_{N1})$ where the differences on the left hand side of the set of equations defines the system matrix A discussed above, and each element of the b matrix is equal to one of the RHS expressions.

In element 340 the new slopes along the x and y axes at each vertex are calculated based on the new geometry. In element 345, the new slopes and/or higher derivatives may be compared to the initial slopes and/or higher derivatives calculated based on the assumed initial geometry of corneal surface 106. If the slopes at the various vertices meet predetermined criteria, then the method 300 may be considered to have converged to a surface shape solution. If the predetermined criteria is not met, then the assumed initial geometry may be updated or modified by the new geometry of corneal surface 106 and elements 330, 335, 340, and 345 repeated until the predetermined criteria is met. The predetermined criteria may include differences between initial and new vertex locations for some or all of the vertices, between initial and new slope for some or all of the vertices, or between initial and new higher derivatives for some or all of the vertices.

In some embodiments, one or more elements 330, 335, 340, and 345 may be modified when these elements are repeated during a subsequent iteration. If more than one iteration is used, one or more modifications of one or more elements 330, 335, 340, and 345 may be used. For example, the predetermined criteria may be modified upon a second iteration or after a predetermined number of iterations. If more than one iteration is used, the predetermined criteria may be modified a plurality of times over different iterations. In certain embodiments, a different polynomial may be used in element 330 of method 300. For example, each vertex may initially be characterized by a second order polynomial. Upon a subsequent iteration of elements 330, 335, 340, and 345 each vertex may be characterized by a third order polynomial. The change may be implemented based on the number of previous iterations or based on some other criteria, for example, based on degree of convergence. In one embodiment, this repetition of iterations of elements 330, 335, 340, and 345 is referred to as polynomial fitting.

In certain embodiments, method 300 or some similar method according to an embodiment of the present invention is incorporated into an algorithm that may be stored in memory 132 shown in FIG. 1. In one embodiment, portions of method 300 are incorporated into a zonal reconstructor module, or reconstructor, and includes at least portions of method 300 related to defining neighborhoods (based on three or more vertices representing the location of three or more of the spot images from the photodetector 140) and local polynomial fitting. In a preferred embodiment, the zonal reconstructor module includes at least portions of method 300 pertaining to Delaunay triangulation and local polynomial fitting. The algorithm or zonal reconstructor module, in some embodiments, is then executed by processor 130 to determine a corneal shape based on spot pattern images produced by light from first and/or second light sources 112, 122 that is reflected off corneal surface 106.

In certain embodiment, a treatment plan for a corneal refractive procedure is produced by processor 130 or by another processor or computer based on the corneal surface 106 profile calculated by an algorithm based on method 300 or some similar method according to an embodiment of the present invention.

In other embodiments, system 100 also includes corneal refractive surgical system 134, wherein system 100 is configured to provide a light pattern image base on light reflected from a corneal surface, calculate a corneal surface profile, calculate a treatment plan from the corneal surface profile, and perform a corneal refractive procedure, for example, by controlling a laser such as an excimer laser, solid state laser, femto second laser, pico second laser, or the like. In some embodiments, corneal refractive surgical system 134 is physically or electronically connected to topographers 111, 121, photodetector 140, and processor 130. In other embodiments, system 100 includes corneal refractive surgical system 134, but there is no direct connection to topographers 111, 121, photodetector 140, and processor 130.

EXAMPLE

Figure 9:
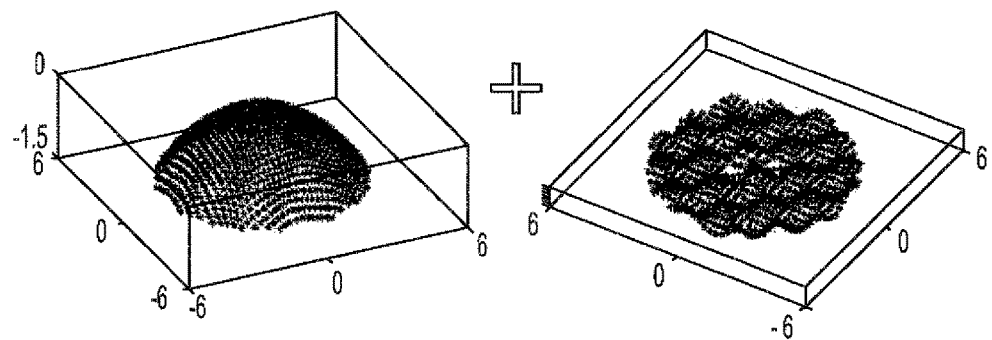
FIG. 9 is an illustration of a sphere surface and a high frequency sinusoidal corrugation profile.
Figure 10:
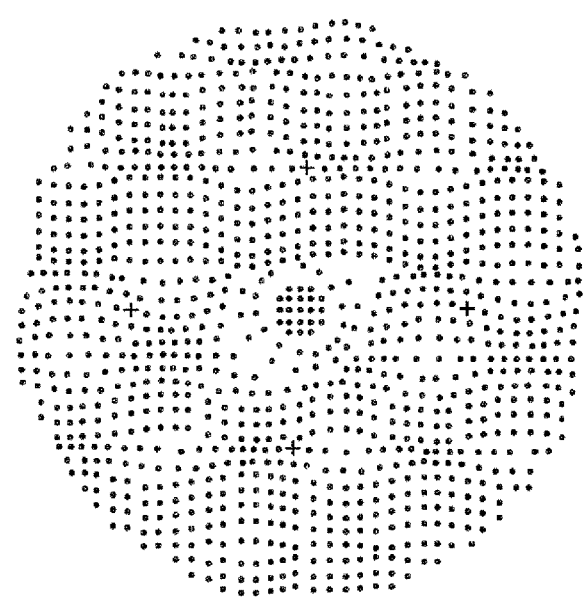
FIG. 10 is a light pattern image corresponding to a model surface based on a combination of the sphere surface and high frequency sinusoidal corrugation profile shown in FIG. 9 in accordance with one embodiment.

Referring to FIGS. 9 and 10, a simulated photodetector image was provided to test an embodiment of the present invention incorporating on the algorithm utilizing method 300 or some similar method according to an embodiment of the present invention. Referring to FIG. 10, a light pattern image is shown that contains high frequency content. The image shown in FIG. 10 is generated by a model surface based on the two elements shown in FIG. 9 (i.e., a spherical surface shown on the left hand side and a high frequency sinusoidal corrugation profile shown on the right hand side). The model surface is the combination of the spherical surface shown on the left side of FIG. 9 and the high frequency sinusoidal corrugation profile shown on the right side of FIG. 9.

The image shown in FIG. 10 was processed using different algorithms and an error from the model surface based on FIG. 9 was calculated in each case. Three different algorithms were tested. The first algorithm was a Zernike modal reconstructor at 6th order. This reconstructor had difficulty capturing the high spatial frequency features of the simulated surface. The RMS error for the Zernike model was 1.47 microns.

The second algorithm was according to an embodiment of the present invention in which each vertex was described by the second order polynomial in Equation (1). Again, this algorithm had difficulty capturing the high spatial frequency features of the simulated surface. The RMS error for the second order algorithm was 1.45 microns.

The third algorithm was according to an embodiment of the present invention in which each vertex was described by the third order polynomial in Equation (3). This algorithm was much better in capturing the high spatial frequency features of the simulated surface. The RMS error for the Zernike model was 0.09 microns, or more that 16 times less than the error produced by the other algorithms. The transition from the second algorithm to the third algorithm is one example of polynomial fitting in accordance with one embodiment of the present invention.

Thus, system 100 is disclosed for determining the shape of ocular surfaces and using the determined shape for treating and/or improving vision of the eye. System 100 allows high spatial frequency artifacts on surfaces (e.g., anterior corneal surface, posterior corneal surface, capsular bag surface, lens, or the like) to be explored via the output shape data. System 100 is also suited for additional specific ophthalmic applications, including but not necessarily limited to, tear film analysis and radial keratotomy (RK) scarring analysis. In addition, the zonal reconstructor may be applied to other paradigms. For example, for splines or radial basis functions, the Delaunay triangulation may be used to determine local neighborhoods with the RHS being altered according to the related model specifics and the system matrix remaining roughly the same.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of shape determination for a surface of an eye, the method comprising the steps of:

directing a pattern of light, from a light source, onto the eye sensing a light pattern, by a photodetector, based on a plurality of images reflected from the surface of the eye, each image corresponding to a location on the surface of the eye; and determining, by a processor, shape data corresponding to the surface of the eye based on a combination of zonal reconstruction and polynomial fitting using the light pattern having the plurality of images, wherein determining shape data comprises:

(a) determining an initial surface location for each of the plurality of images;

(b) calculating initial values for one or more derivatives for each initial surface location;

(c) forming a plurality of neighborhoods, each neighborhood comprising a set of vertices corresponding to a set of initial surface locations;

(d) forming a system matrix including all vertices contained in each neighborhood;

(e) characterizing each vertex contained in each neighborhood by a mathematical relationship which is a polynomial function including a plurality of parameter coefficients;

(f) calculating values for each of the plurality of parameter coefficients based on the mathematical relationships of the vertices for all the neighborhoods;

(g) based on the system matrix and the values for the parameter coefficients, calculating one or more new surface locations for at least some of the vertices and new values for at least some of the one or more derivatives for each new surface location;

(h) comparing one or more of the new values for at least some of the one or more derivatives with the initial values for one or more derivatives and the one or more new surface locations with the initial surface locations; and (i) if the comparison meets a predetermined criteria, outputting the shape data, the shape data comprising one or more of: at least some of the initial surface locations, at least some of the initial values for one or more derivatives, at least some of the one or more new surface locations, and at least some of the new values for at least some of the one or more derivatives; or if the comparison does not meet the predetermined criteria:

replacing one or more of the initial surface locations with one or more of the one or more new surface locations and replacing the one or more initial values for one or more derivatives with one or more of the new values for at least some of the one or more derivatives; and repeating steps (e), (f), (g), (h), and (i).

2. The method of claim 1, further comprising filtering unwanted neighborhoods from the plurality of neighborhoods after step (c) and before step (d).

3. The method of claim 2, wherein each neighborhood of the plurality of neighborhoods comprises a triangle of vertices, and wherein the filtering unwanted neighborhoods comprises:

determining a subset of neighborhoods of the plurality of neighborhoods that have an angle less than a predetermined angle; and replacing at least some of the neighborhoods of the subset of neighborhoods with a different neighborhood, the different neighborhood lacking the angle less than the predetermined angle.

4. The method of claim 1, wherein the forming a plurality of neighborhoods comprises a Delaunay triangulation of the vertices.

* * * * *